United States Patent [19]
Pirola et al.

[11] Patent Number: 6,080,872
[45] Date of Patent: Jun. 27, 2000

[54] CYCLOALIPHATIC EPOXY COMPOUNDS

[75] Inventors: Roberto Pirola, Dalmine; Carlo Fumagalli, Albano S. Alessandro; Giuseppe Caramaschi, Bologna, all of Italy; Christian Beisele, Auggen, Germany

[73] Assignee: Lonza S.P.A., Mailand, Italy

[21] Appl. No.: 09/331,201
[22] PCT Filed: Dec. 16, 1997
[86] PCT No.: PCT/EP97/07075
§ 371 Date: Sep. 16, 1999
§ 102(e) Date: Sep. 16, 1999
[87] PCT Pub. No.: WO98/27099
PCT Pub. Date: Jun. 25, 1998

[51] Int. Cl.$^7$ .................................................. C07D 491/00
[52] U.S. Cl. ............................................. 548/431; 528/365
[58] Field of Search .............................. 548/431; 528/365

[56] References Cited

U.S. PATENT DOCUMENTS 3,369,055  2/1968  Salyer et al. ............................... 528/96
3,450,711  6/1969  Megna et al. .............................. 548/423

OTHER PUBLICATIONS

Monte et al., Macromolecular Chemistry and Physics, vol. 196, No. 4, (1995), pp 1051–62.
*Patent Abstracts Of Japan*, vol. 4, No. 124, (C–023), (Sep. 2, 1980).
Storey et al., Journal of Polymer Science, Part A: Polymer Chemistry, vol. 31, No. 6, (1993), pp. 1825–1838.

*Primary Examiner*—Fiona T. Powers
*Attorney, Agent, or Firm*—Fisher, Christen & Sabol

[57] ABSTRACT

Cycloaliphatic epoxy compounds represented by general formula (I):

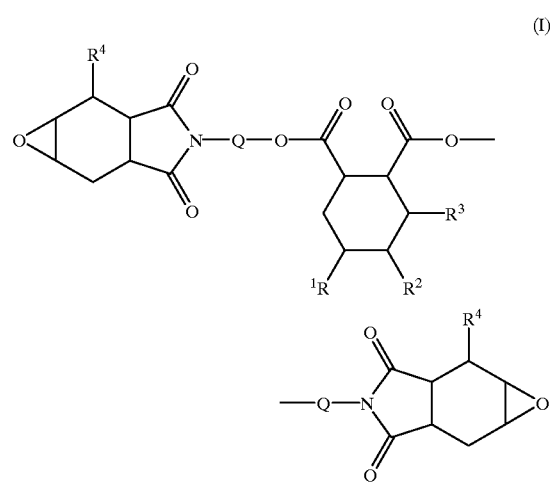

wherein $R^1$ and $R^2$ are hydrogen atoms, or $R^1$ and $R^2$ taken together represent an epoxy group, $R^3$ and $R^4$ are the same or different and each represents a hydrogen atom or a methyl group, and Q is a linear or branched alkanediyl group with 2 to 16 carbon atoms and with the proviso that the adjacent nitrogen and oxygen atoms are not attached to the same carbon atom. The cycloaliphatic epoxy compounds can be used to produce cured epoxy resin compositions exhibiting superior mechanical properties, e.g., tensile and flexural strength and toughness.

25 Claims, No Drawings

CYCLOALIPHATIC EPOXY COMPOUNDS

This application is a 371 of PCT/EP97/07075 filed Dec. 16, 1997.

This invention relates to novel cycloaliphatic epoxy compounds. It further relates to a process for preparing such epoxy compounds, a cured epoxy resin derived therefrom, and a process for preparing such cured epoxy resin.

Cycloaliphatic epoxy resins are epoxy resins resulting from epoxidation of cycloaliphatic olefins. These resins usually exhibit better mechanical and electrical properties than the common glycidyl ether epoxy resins. Some of their properties, however, are not completely satisfactory. In particular they are very rigid and brittle and not as tough as one would wish.

It is a purpose of the present invention to provide cycloaliphatic epoxy resins which exhibit improved fracture-mechanical properties, in particular high toughness (as expressed by the critical stress intensity factor, $K_{1C}$, and the specific fracture energy, $G_{1C}$) as well as high strength.

According to the invention, this objective is accomplished by the cycloaliphatic epoxy compounds of the general formula

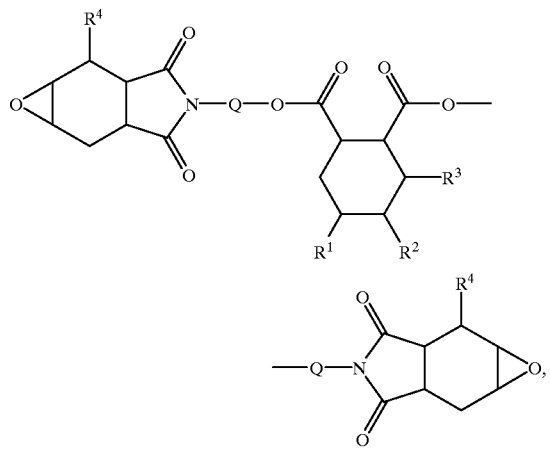

I wherein $R^1$ and $R^2$ are hydrogen atoms, or $R^1$ and $R^2$ taken together represent an epoxy group; $R^3$ and $R^4$ are the same or different and each represents a hydrogen atom or a methyl group; and Q is a linear or branched alkanediyl group with 2 to 16 carbon atoms and with the proviso that the adjacent nitrogen and oxygen atoms are not attached to the same carbon atom.

Preferably, the residues $R^3$ and $R^4$ are hydrogen atoms.

According to the invention, the new cycloaliphatic epoxy compounds can be prepared by (i) reacting an acid or an ester of the general formula

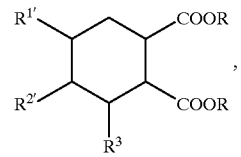

II wherein R is hydrogen or a $C_{1-6}$-alkyl group, $R^{1'}$ and $R^{2'}$ are hydrogen atoms, or $R^{1'}$ and $R^{2'}$ taken together represent a direct bond between the adjacent carbon atoms, and $R^3$ is a hydrogen atom or a methyl group, in the presence of a catalyst with a N-(hydroxyalkyl)-tetrahydrophthalimide of the general formula

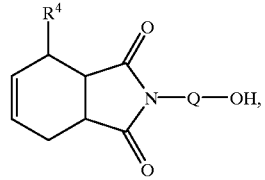

III wherein $R^4$ is hydrogen or a methyl group and Q is as described above, to form an unsaturated compound of the general formula

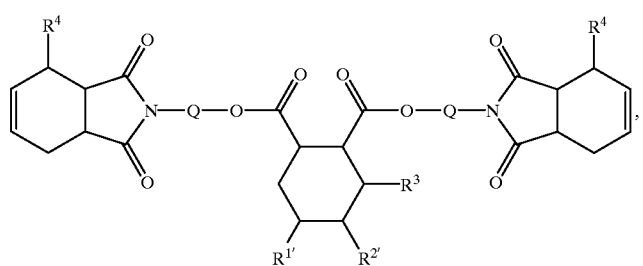

IV wherein $R^{1'}$, $R^{2'}$, $R^3$, $R^4$ and Q are as defined above, and (ii) epoxidizing said unsaturated compound (IV) by reacting it with a peroxy compound.

The acids and esters (II) are known compounds. The tetrahydro- and hexahydrophthalic acids and anhydrides are commercially available. The esters are commercially available too or easily prepared from the corresponding acids or anhydrides.

Preferably the isobutyl esters are used as starting materials.

The N-(hydroxyalkyl)tetrahydrophthalimides (III) are known compounds and commercially available or easily prepared from the corresponding tetrahydrophthalic acids or anhydrides and the corresponding aminoalcohols $H_2N-Q-OH$. Preferably N-(hydroxyalkyl) tetrahydrophthalimides (III) wherein Q is $-(CH_2)_n-$ and n is a whole number from 2 to 16 are employed. Most preferably, Q is $-(CH_2)_2-$.

The first step, which is an esterification or a transesterification, may be performed in an inert solvent or, preferably, without solvent. Advantageously, the water or alcohol R—OH formed as a byproduct is distilled off during the reaction to shift the equilibrium in the desired direction. Standard catalysts (e. g. strong acids) may be used in this step.

As a peroxy compound, both organic and inorganic peroxy compounds may be used. Preferably peroxycarboxylic acids are used as peroxy compounds, monoperphthalic acid being especially preferred.

Hydrogen peroxide is also a preferred peroxy compound. When hydrogen peroxide is used, a phase transfer catalyst may be used. Examples of suitable phase transfer catalysts are described in: *J Polym. Sci., Part A: Polym. Chem.* 1993, 31, 1825–1938.

The epoxidation reaction is advantageously carried out in an inert solvent. Suitable inert solvents are, for example, alkyl esters, halogenated hydrocarbons, cycloaliphatic hydrocarbons, aromatic hydrocarbons or alcohols.

The cycloaliphatic epoxy compounds according to the invention can be used alone or in combination with other epoxy compounds to manufacture cured epoxy resins by reacting with common curing agents. The curing agents may include catalysts such as e. g. amines or ammonium salts, imidazoles, boron trihalide-amine adducts, sulfonium salts, or photoactive initiators such as triarylsulfonium salts, diaryliodonium salts, diazonium salts, or iron-arene complexes.

Preferably dicarboxylic acid anhydrides are used as curing agents. Especially preferrred are cycloaliphatic dicarboxylic acid anhydrides such as hexahydrophthalic anhydride and methylhexahydrophthalic anhydride.

Cured epoxy resin compositions containing the new cycloaliphatic epoxy compounds can be prepared by (i) mixing the cycloaliphatic epoxy compounds according to the invention with a curing agent and (ii) curing the thus obtained composition by subjecting it to heat for a sufficient time at a suitable temperature to obtain a cured composition. Optionally, one or more additional epoxy compounds, solvents, plasticizers, fillers and/or pigments may be added. Preferably the additional epoxy compounds are cycloaliphatic epoxy compounds too.

The invention will be further described based on the following non-limiting examples.

EXAMPLE 1

Bis[2-(1,2,3,6-tetrahydrophthalimido)ethyl] 1,2,3,6-tetrahydrophthalate {=Bis[2-(1,3,3a,4,7,7a-hexahydro-1,3-dioxo-2H-isoindol-2-yl)ethyl} 4-cyclohexene-1,2-dicarboxylate]

(IV, $R^{1'},R^{2'}$=bond, $R^3=R^4=H$, Q=$-(CH_2)_2-$)

N-(2-Hydroxyethyl)-1,2,3,6-tetrahydrophthalimide (195.2 g, 1 mol) was dissolved in diisobutyl 1,2,3,6-tetrahydrophthalate (141.2 g, 0.5 mol). The mixture was kept at 150° C. under vacuum to eliminate any traces of water. Titanium tetrabutoxide (1.7 g) was added under atmospheric pressure and the transesterification reaction was carried out distilling off the isobutyl alcohol formed. As the reaction proceeded the temperature was increased stepwise to 230° C. and the pressure was lowered to 20 Torr (26.7 mbar). After ca. 24 h, 265 g of brown crude bis[2-(1,2,3,6-tetrahydrophthalimido)ethyl] 1,2,3,6-tetrahydrophthalate were obtained.

Iodine number: 137 (calcd.: 145)
Acid number: 0
Viscosity at 100° C.: 1000 mPa.s

EXAMPLE 2

Bis[2-(1,2,3,6-tetrahydrophthalimido)ethyl] hexahydrophthalate [=Bis[2-1,3,3a,4,7,7a-hexahydro-1,3-dioxo-2H-isoindol-2-yl)ethyl] 1,2-cyclohexanedicarboxylate]

(IV, $R^{1'}=R^{2'}=R^3=R^4=H, Q=-(CH_2)_2-$)

N-(2-Hydroxyethyl)-1,2,3,6-tetrahydrophthalimide (195.2 g, 1 mol) was dissolved in diisobutyl hexahydrophthalate (142.2 g, 0.5 mol). The mixture was treated as described in example 1 to obtain 266 g of brown crude bis[2-(1,2,3,6-tetrahydrophthalimido)ethyl] hexahydrophthalate.

Iodine number: 92 (calcd.: 96)
Acid number: 0
Viscosity at 100° C.: 650 mPa.s

EXAMPLE 3

Bis[2-(4,5-epoxyhexahydrophthalimido)ethyl] 4,5-epoxyhexahydrophthalate {=Bis[2-(octahydro-3,5-dioxo-4H-oxireno[f]isoindol-4-yl)ethyl] 7-oxabicyclo[4.1.0[heptane-3,4-dicarboxylate}

(I,$R^1,R^2=R^3=-O-,R^4=H$, Q=$-(CH_2)_2-$)

Crude bis[2-( 1,2,3,6-tetrahydrophthalimido)ethyl] 1,2,3, 6-tetrahydrophthalate (185 g, 0.33 mol) was dissolved in 370 g of ethyl acetate at 50° C. Solid monoperphthalic acid (95% purity, 250 g, 1.3 mol) was added portionwise during 1 h. By immersing the reaction flask in cold water the temperature of the stirred reaction mixture was maintained at 50° C.

When the exothermic reaction ceased, the flask was immersed in a warn bath and the reaction mixture was allowed to stand at 50° C. for another 2 h. After cooling to room temperature, the reaction mixture was filtered and the solid washed with 250 g of ethyl acetate. The filtrate was treated with aqueous sodium carbonate until its acid number was less than 1 mg KOH/g and then washed with water. The organic layer was concentrated in vacuo and dried at 80° C./10 Torr (13.3 mbar) to give 173 g of solid bis[2-(4,5-epoxyhexahydrophthalimido)ethyl] 4,5-epoxyhexahydrophthalate.

Iodine number: <1
Oxirane content: 7.2 wt. %
Acid number: <1 mg KOH/g
Yield: 78%

EXAMPLE 4

Bis[2-(4,5-epoxyhexahydrophthalimido)ethyl] hexahydrophthalate [=Bis[2-(octahydro-3,5-dioxo-4H-oxireno[f]isoindol-4-yl)ethyl] 1,2-cyclohexanedicarboxylate]

(I, $R^1=R^2=R^3=H$, $Q=-(CH_2)_2-$)

Crude bis[2-(1,2,3,6-tetrahydrophthalimido)ethyl] hexahydrophthalate (278 g, 0.5 mol) was dissolved in 556 g of ethyl acetate at 50° C. Solid monoperphthalic acid (95% purity, 250 g, 1.3 mol) was added portionwise during 1 h. The further procedure and workup was carried out as described in example 3 to give 280 g of bis[2-(4,5-epoxyhexahydrophthalimido)ethyl] hexahydrophthalate as a solid.

Iodine number: 0.3
Oxirane content: 5.2 wt. %
Acid number: 0.6 mg KOH/g
Yield: 91%

EXAMPLE 5

Bis[2-(4,5-epoxyhexahydrophthalimido)ethyl] 4,5-epoxyhexahydrophthalate [=Bis[2-(octahydro-3,5-dioxo-4H-oxireno[f]isoindol4-yl)ethyl] 7-oxabicyclo[4.1.0]heptane-3,4-dicarboxylate]

(I,$R^1,R^2=-O-,R^3=R^4=H$, $Q=-(CH_2)_2-$)

Crude bis[2-(1,2,3,6-tetrahydrophthalimido)ethyl] 1,2,3,6-tetrahydrophthalate (185 g, 0.33 mol) was dissolved in 463 g of xylenes at 65° C. To the solution was added Aliquat® 336 (1.8 g) and then dropwise, within 10 min, a solution of sodium tungstate dihydrate (16.6 g) and phosphoric acid (34%, 38 g) in aqueous hydrogen peroxide (20%, 211 g, 1.24 mol). By immersing the reaction flask in cold water the temperature of the stirred reaction mixture was maintained at 65° C. When the exothermic reaction ceased, the flask was immersed in a warm bath and the reaction mixture was allowed to stand at 65° C. for another 3 h. After cooling to room temperature, the layers were separated, and the organic layer was dried. The solvent was removed in vacuo and the residue dried at 80° C./10 Torr (13.3 mbar) to give 176 g of bis[2-(4,5-epoxyhexahydrophthalimido)ethyl] 4,5-epoxyhexahydrophthalate as a solid Iodine number: <1
Oxirane content: 6.5 wt. %
Acid number: <1 mg KOH/g
Yield: 71.5%

EXAMPLE 6

Bis[2-(4,5-epoxyhexahydrophthalimido)ethyl] hexahydrophthalate [=Bis[2-(octahydro-3,5-dioxo-4H-oxireno[f]isoindol-4-yl)ethyl] 1,2-cyclohexanedicarboxylate]

(I,$R^1=R^2=R^3=R^4=H,Q=-(CH_2)_2-$)

Crude bis[2-(1,2,3,6-tetrahydrophthalimido)ethyl] hexahydrophthalate (278 g, 0.5 mol) was dissolved in 695 g of xylenes at 65° C. To the solution was added Aliquat® 336 (2.8 g) and then dropwise, within 10 min, a solution of sodium tungstate dihydrate (16.6 g) and phosphoric acid (34%, 38 g) in aqueous hydrogen peroxide (20%, 211 g, 1.24 mol). The further procedure and workup was carried out as described in example 5 to give 301 g of bis[2-(4,5-epoxyhexahydrophthalimido)ethyl] hexahydrophthalate as a solid.

Iodine number: <1
Oxirane content: 4.5 wt. %
Acid number: <1 mg KOH/g
Yield: 85%

EXAMPLE 7

Preparation of a cured epoxy resin from bis[2-(4,5-epoxyhexahydrophthalimido)-ethyl] hexahydrophthalate (with filler)

In a mixing vessel with heating equipment bis[2-(4,5-epoxyhexahydrophthalimido)ethyl] hexahydrophthalate (111.8 g, 0.20 mol) was mixed with (3,4-epoxycyclohexyl)methyl 3,4-epoxycyclohexanecarboxylate (Araldite® CY-179, 111.8 g, 0.44 mol) and heated up to 80° C. Within 20 min, a homogeneous solution formed. Hexahydrophthalic anhydride (175.4 g, 1.14 mol) was liquified and added to the mixture of epoxy compounds. After a short mixing, tetramethylammonium chloride (1 g of 30% soln. in methanol) was added and mixed in for a short time. Then 600 g of silica powder (type W12, Quarzwerke, Germany) was added. The mixture then was heated up to 80° C. under stirring and stirred for another 30 min in vacuo (10 mbar). After that, it was filled in flat moulds which had been treated with a mould release agent (QZ 13, Ciba-Geigy Ltd., Switzerland) and preheated to 80° C. The resin was cured by keeping at 80° C. for 8 h and, subsequently, at 140° C. for 10 h. After curing, test bars (80×34×4 mm$^3$) were prepared by cutting and subjected to mechanical and thermomechanical testing. The critical stress intensity factors and the specific fracture energies were measured in double-torsional experiments using test bars with a longitudinal 1 mm deep 60° V-groove.

EXAMPLE 8

Preparation of a cured epoxy resin from bis[2-(4,5-epoxyhexahydrophthalimido)-ethyl] 4,5-epoxyhexahydrophthalate (with filler)

In a mixing vessel with heating equipment bis[2-(4,5-epoxyhexahydrophthalimido)ethyl] 4,5-epoxyhexahydrophthalate (105.4 g, 0.20 mcl) was mixed with (3,4-epoxycyclohexyl)-methyl 3,4-epoxycyclohexanecarboxylate (Araldite® CY-179, 105.4 g) and heated up to 80° C. Within 20 min, a homogeneous solution formed. Hexahydrophthalic anhydride (188.1 g) was liquified and added to the mixture of epoxy compounds. After a short mixing, tetramethylammonium chloride (1.07 g of 30% soln. in methanol) was added and mixed in for a short time. Then 600 g of silica powder (type W12, Quarzwerke, Germany) was added. The mixture then was heated up to 80° C. under stirring and stirred for another 30 min in vacuo (10 mbar). After that, it was filled in flat moulds which had been treated with a mould release agent (QZ 13, Ciba-Geigy Ltd., Switzerland) and preheated to 80° C. The resin was cured by keeping at 80° C. for 8 h and, subsequently, at 140° C. for 10 h and 180° C. for 2 h. After curing, test bars were prepared by cutting and subjected to mechanical and thermomechanical testing.

EXAMPLE 9

Preparation of a cured epoxy resin from bis[2-(4,5-epoxyhexahydrophthalimido)-ethyl] 4,5-epoxyhexahydrophthalate (without filler)

The procedure of Example 8 was repeated without addition of silica.

Comparative Example A (with filler)

The procedure of example 7 was repeated using 210.7 g (1.37 mol) of hexahydrophthalic anhydride, 188.1 g (0.75 mol) of (3,4-epoxycyclohexyl)methyl 3,4-epoxycyclohexanecarboxylate as the sole epoxy compound, and 1.2 g of tetramethylammonium chloride solution.

Comparative Example B (without filler)

The procedure was the same as in comparative example A, but without addition of silica.

For the cured epoxy compositions containing silica, the glass transition temperature $T_g$, the coefficient of thermal expansion, and the mechanical properties have been determined. The results of the mechanical and thermomechanical tests are compiled in table 1.

TABLE 1

| Sample | Ex. 7 | Ex. 8 | Comp. A |
|---|---|---|---|
| $T_g$ [° C.][1] | 168 | 195 | 187 |
| Coefficient of thermal expansion [$10^{-6}$/K.] (DIN 53752/80) | 35.4 | 33.3 | 38.8 |
| Tensile strength [MPa] (ISO R 527) | 85.4 | 70.3 | 63.8 |
| Elongation (ISO R 527) | 0.91% | 0.72% | 0.70% |
| Tensile modulus [MPa] (ISO R 527) | 11210 | 10920 | 9973 |
| Flexural strength [MPa] (ISO 178) | 117.1 | 111.5 | 96.3 |
| Strain of outer fibre (ISO 178) | 1.07% | 1.03% | 0.97% |
| Flexural modulus [MPa] (ISO 178) | 11340 | 11300 | 10300 |
| $K_{IC}$ [MPa · m½][2] | 1.83 | 1.64 | 1.56 |
| $G_{IC}$ [J/m²][3] | 268 | 215 | 214 |

[1]Glass transition temperature, measured with a thermo-mechanical analyser (Mettler TA 4000)
[2]Critical stress intensity factor, measured with a tensile-pressure-machine (class 1 according to DIN 51221)
[3]Specific fracture energy, measured with a tensile-pressure-machine (class 1 according to DIN 51221)

The compositions according to the invention exhibit significantly higher tensile and flexural strength and toughness as compared to the composition according to the prior art. They also have significantly lower coefficients of thermal expansion.

For the unfilled compositions of example 9 and comparative example B, the coefficients of thermal expansion and the electrical insulating properties have been determined. The results are given in table 2.

TABLE 2

| Sample | Ex. 9 | Comp. Ex. B |
|---|---|---|
| Coefficient of thermal expansion [$10^{-6}$/K.] (DIN 53752/80) | 58.3 | 68.6 |
| Tracking resistance[1] (IEC 112/79) [V\|mm] | >600\|0.1 | >600\|0.5 |
| Arc resistance [s] (ASTM-D 495) | 193–194 | 130–180 |

[1]measured with wetting agent, tracking voltage and depth of erosion given

Besides the reduction in the coefficient of thermal expansion, the composition according to the invention exhibits a better tracking resistance (smaller depth of erosion) and an improved arc resistance.

What is claimed is:

1. Cycloaliphatic epoxy compounds represented by the general formula

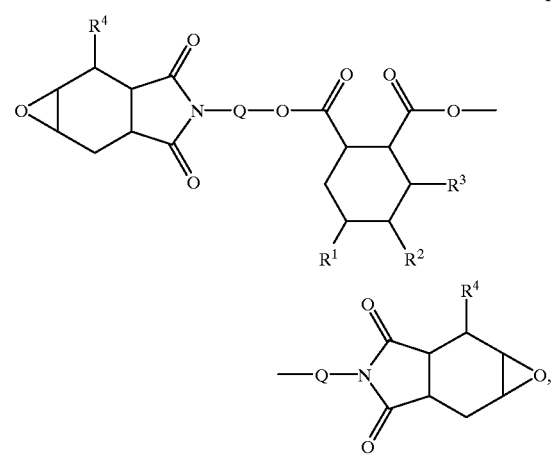

wherein $R^1$ and $R^2$ are hydrogen atoms, or $R^1$ and $R^2$ taken together represent an epoxy group;

$R^3$ and $R^4$ are the same or different and each represents a hydrogen atom or a methyl group;

and Q is a linear or branched alkanediyl group with 2 to 16 carbon atoms and with the proviso that the adjacent nitrogen and oxygen atoms are not attached to the same carbon atom;

and mixtures thereof.

2. Cycloaliphatic epoxy compounds according to claim 1, wherein $R^3$ and $R^4$ are hydrogen atoms.

3. Cycloaliphatic epoxy compounds according to claim 2, wherein Q is —$(CH_2)_n$— and n is a whole number from 2 to 16.

4. Cycloaliphatic epoxy compounds according to claim 3, wherein Q is —(CH$_2$)$_2$—.

5. Cycloaliphatic epoxy compounds according to claim 1, wherein Q is —(CH$_2$)$_n$— and n is a whole number from 2 to 16.

6. A process for producing a cycloaliphatic epoxy compound represented by the general formula

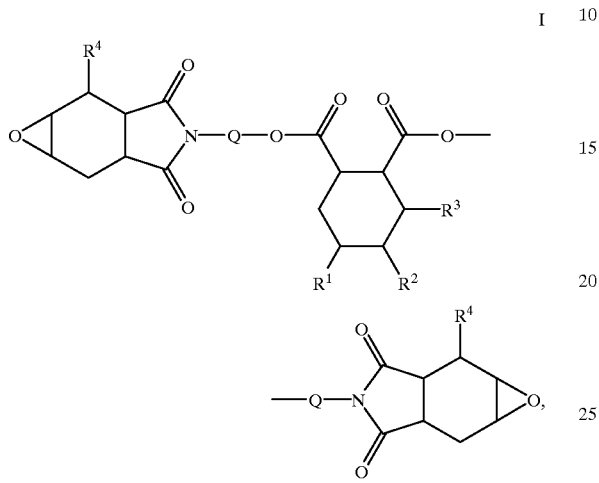

wherein R$^1$ and R$^2$ are hydrogen atoms, or R$^1$ and R$^2$ taken together represent an epoxy group;

R$^3$ and R$^4$ are the same or different and each represents a hydrogen atom or a methyl group;

and Q is a linear or branched alkanediyl group with 2 to 16 carbon atoms and with the proviso that the adjacent nitrogen and oxygen atoms are not attached to the same carbon atom;

which process comprises the steps of (i) reacting an acid or ester of the general formula

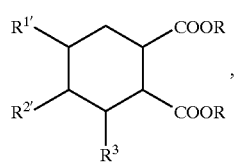

wherein R is a hydrogen atom or a C$_{1-6}$-alkyl group; R$^{1'}$ and R$^{2'}$ are hydrogen atoms, or R$^{1'}$ and R$^{2'}$ taken together represent a direct bond between the adjacent carbon atoms; and R$^3$ is a hydrogen atom or a methyl group; in the presence of a catalyst with a N-(hydroxyalkyl)tetrahydrophthalimide of the general formula

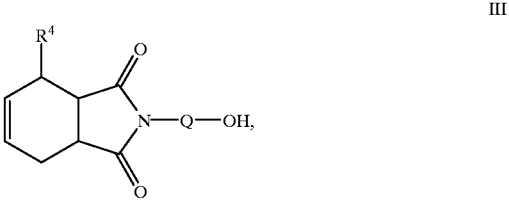

wherein R$^4$ is hydrogen or a methyl group and Q is as mentioned above, to form an unsaturated compound of the general formula

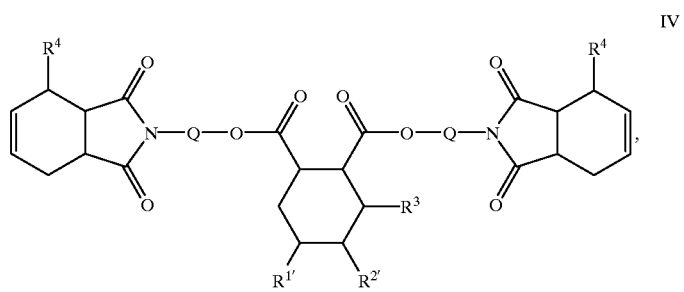

wherein R$^{1'}$, R$^{2'}$, R$^3$, R$^4$ and Q are as defined above, and
(ii) epoxidizing said unsaturated compound (IV) by reacting it with a peroxy compound.

7. A process according to claim 6, wherein R is isobutyl.

8. A process according to claim 7, wherein R$^3$ and R$^4$ are hydrogen atoms.

9. A process according to claim 8, wherein Q is —(CH$_2$)$_n$— and n is a whole number from 2 to 16.

10. A process according to claim 9, wherein Q is —(CH$_2$)$_2$—.

11. A process according to claim 10, wherein the peroxy compound is a peroxycarboxylic acid.

12. A process according to claim 11, wherein the peroxycarboxylic acid is monoperphthalic acid.

13. A process according to claim 10, wherein the peroxy compound is hydrogen peroxide.

14. A process according to claim 6, wherein R$^3$ and R$^4$ are hydrogen atoms.

15. A process according to claim 6, wherein Q is —$(CH_2)_n$— and n is a whole number from 2 to 16.

16. A process according to claim 6, wherein the peroxy compound is a peroxycarboxylic acid.

17. A process according to claim 6, wherein the peroxy compound is hydrogen peroxide.

18. A cured epoxy resin obtainable by cross-linking a cycloaliphatic epoxy compound as claimed in claim 1 and, optionally, one or more additional epoxy compounds with a curing agent.

19. A cured epoxy resin obtainable by cross-linking a cycloaliphatic epoxy compound as claimed in claim 4 and, optionally, one or more additional epoxy compounds with a curing agent.

20. A cured epoxy resin according to claim 19, wherein the curing agent is a dicarboxylic acid anhydride.

21. A cured epoxy resin according to claim 20, wherein the dicarboxylic acid anhydride is a cycloaliphatic dicarboxylic acid anhydride.

22. A process for preparing a cured epoxy resin composition, which process comprises the steps of (i) mixing a cycloaliphatic epoxy compound as claimed in claim 4 with a curing agent and, optionally, one or more additional epoxy compounds, solvents, plasticizers, fillers, and/or pigments and (ii) curing the thus obtained composition by subjecting it to heat for a sufficient time at a suitable temperature to obtain a cured composition.

23. A process according to claim 22, wherein the curing agent is a dicarboxylic acid anhydride.

24. A process according to claim 23, wherein the dicarboxylic acid anhydride is a cycloaliphatic dicarboxylic acid anhydride.

25. A process for preparing a cured epoxy resin composition, which process comprises the steps of (i) mixing a cycloaliphatic epoxy compound as claimed in claim 1 with a curing agent and, optionally, one or more additional epoxy compounds, solvents, plasticizers, fillers, and/or pigments, and (ii) curing the thus obtained composition by subjecting it to heat for a sufficient time at a suitable temperature to obtain a cured composition.

* * * * *